United States Patent [19]
Kumar

[11] Patent Number: 5,885,769
[45] Date of Patent: Mar. 23, 1999

[54] SCREENING SYSTEMS

[75] Inventor: Chanakanti Chandra Kumar, Edison, N.J.

[73] Assignee: Schering Corporation, Kenilworth, N.J.

[21] Appl. No.: 735,068

[22] Filed: Jul. 24, 1991

Related U.S. Application Data

[63] Continuation-in-part of Ser. No. 655,966, Feb. 14, 1991, abandoned.

[51] Int. Cl.$^6$ .............................. C12Q 1/68; C12Q 1/70; C12N 5/10; C12N 15/86
[52] U.S. Cl. .................................. 435/5; 435/6; 435/7.1; 435/29; 435/7.6; 435/455; 435/456; 435/465; 435/467; 435/325; 435/353; 435/320.1; 536/23.1; 536/23.2; 536/23.5; 536/24.1
[58] Field of Search ............................... 435/4, 6, 7.23, 435/69.1, 29, 34, 55, 70, 71, 5, 7.1, 7.6, 455, 456, 466, 467, 325, 353, 320.1, 23.1, 23.2, 23.5, 24.1; 536/23.1, 23.2, 23.5, 24.1

[56] References Cited

PUBLICATIONS

Kedar et al. "Transfected human B–polymerase..." Mol Cell. Bio 10: 3852–3856 1990.
Lenardo et al. "Suppression of MHC class Z..." EMBO 8: pp. 3351–3355 1989.
Avvedimento, V. et al, "Neoplastic transtormation inactivate..." Proc. Natl. Mod. Sci. vol. 85, pp. 1744–1748 Mar. 1988.
Bernstem et al, "Alzljun Farction is differentially..." Science vol. 244 pp. 566–569.
Shindo–Okoda et al. "Permanent Conversion of HlH3T3..." in Antlmutogives L Anticacogives... ed. Kuroda et al. pp.309–,312, 1990.
Nakaro et al. "Transcriptional regulatory..." Gene 99 , pp. 285–289 , 1991.
An et al., Mol., Cell. Biol. 2: 1628 (1982).
Bishop et al., Ann, Rev. Biochem. 52: 301 (1983).
Corjay et al., J. Biol. Chem. 264: 10501 (1989).
DeWet et al., Mol. Cell. Biol. 7:725 (1987).
Franza et al., Cancer 1:137 (1984).
Gorman et al., Mol. Cell. Biol. 2:1044 (1982).
Henthorn et al., Proc. Natl. Acad. Sci. USA 85:6342 (1988).
Kumar et al., Biochemistry 28:4027 (1989).
Kumar et al., in Cytoskeletal Proteins in Tumor Diagnosis, 1989, Weber et al., Eds., Cold Spring Harbor Press, pp. 91–97.
Leavitt et al., Nature 316:840 (1985).
Owen et al., Mol. Cell. Biol. 10:1 (1990).
Owens et al., J. Cell Biol. 102:343(1988).
Pollack et al., Proc. Natl. Acad. Sci. USA 72:994 (1975).
Reddy et al., J. Biol. Chem. 265:1683 (1990).
Searle et al., Mol. Cell. Biol. 5:1480 (1985).
Shumperli et al., Proc. Natl. Acad. Sci. USA 79:257. (1982).
Topp, Virology 113:408 (1981).
Tsang et al., Proc. Natl. Acad. Sci. USA 85:8598 (1988).
Weinberg et al., Science 230:770 (1985).
Whyte et al., Nature 334:124 (1988).
R&D Synapse, vol., 3 No. 4, Apr. 1990, pp. 5–6.

*Primary Examiner*—David Guzo
*Attorney, Agent, or Firm*—James M. Gould; Norman C. Dulak

[57] ABSTRACT

Transformed cell lines containing a reporter gene operatively linked to a genetic control element that is responsive to growth factor-stimulated cell proliferation and/or oncogene-mediated neoplastic transformation are provided. Also provided are methods for using such transformed cell lines to screen for growth factor antagonists and/or antineoplastic agents.

40 Claims, 5 Drawing Sheets

SCREENING SYSTEMS

This is a continuation-in-part of application Ser. No. 07/655,966, filed Feb. 14, 1991, now abandoned.

TECHNICAL FIELD

This invention relates to recombinant vectors comprising genetic control elements that are sensitive to the stimulation of cell division by growth factors and/or to oncogene-mediated neoplastic transformation. This invention further relates to recombinant vectors comprising such genetic control elements operatively linked to reporter genes, cells stably transformed with such vectors, and methods for using such transformed cells to identify antagonists of growth factors and/or oncogene-mediated neoplastic transformation.

BACKGROUND OF THE INVENTION

Most screening systems currently used to identify potential antineoplastic drugs evaluate the ability of compounds to kill rapidly-growing cells in culture. Drugs identified in such systems are thus generally not specific for tumor cells but are also toxic to rapidly-growing normal cells in the body. Out of more than 400,000 compounds that have been evaluated in such systems, fewer than twenty have shown an acceptably low level of toxicity, and even these compounds show toxic effects in most cancer patients.

More effective cancer chemotherapy will require the identification of new drugs that act to specifically kill cancer cells or to suppress the transformed phenotype, while exhibiting low toxicity to normal cells. To find these new drugs, new screening systems will be required.

Our understanding of the molecular basis of cancer has been revolutionized by the identification of a relatively small set of normal cellular genes called protooncogenes which, when altered, can produce neoplastic change [Bishop, Ann. Rev. Biochem. 52:301 (1983); Varmus, Ann. Rev. Genetics 18:553 (1984)]. Alterations in protooncogene expression can occur for a variety of reasons, including mutations, nucleotide substitutions, chromosomal translocations, gene amplifications, and the insertion of mobile genetic elements. As a result of such changes, the expression of protooncogenes may be altered or they may be mutated to encode altered protein products.

The proteins encoded by protooncogenes play an important role in governing many aspects of cell growth and development. Mutant or activated protooncogenes are believed to make specific contributions to the phenotypes of tumor cells and hence are called oncogenes.

One of the remarkable features of cellular protooncogenes is that they have shown extraordinary conservation during evolution. Several of these genes have been identified in organisms as diverse as yeast, mammals, birds, fish and insects. This evolutionary conservation suggests that the proteins encoded by the protooncogenes must have important functions in normal cell growth and development, with each directing a particular event in the complex system of signals that regulates the proliferation and differentiation of cells. Changes in any one or more of these genes can lead to cancer (Bishop, supra; Varmus, supra).

The proteins encoded by protooncogenes fall into several groups. Some are growth factors—polypeptides that signal cells to divide. Others are receptors for growth factors, molecules that are embedded in the cell membranes and respond to growth factors. Another group is known as the group of G proteins, which transmit signals from receptors to other components of the signal-transduction pathway. Others are protein kinases which phosphorylate other proteins. Still others are nuclear proteins that are involved in DNA transcription [Weinberg, Science 230:770 (1985)]. A schematic representation of the pathway by which signals generated outside a cell can transmit information to the nucleus to produce cell division is shown in FIG. 1.

More recent research has focused on the part played by negative regulators of cell growth in the development of cancer. These negative regulators are known as tumor suppressor genes (also known as recessive oncogenes or anti-oncogenes). Unlike oncogenes of viral and cellular origin, which appear to act in a dominant manner to confer transformed characteristics, loss of both copies of these recessive oncogenes is required for neoplastic change [Stanbridge, Bioessays 3:252 (1985)].

A protein called the Rb protein which is encoded by one such anti-oncogene, the retinoblastoma anti-oncogene, is presumed to act in the control of the cell cycle. Oncogenes carried by DNA tumor viruses such as SV-40 large T antigen and adenovirus EIA function by complexing with and inactivating the Rb protein [Whyte, et al., Nature 334:124 (1988)].

Although oncogenes have been linked to tumor growth, the signalling pathways controlled by oncogene proteins are not limited to growth control alone. Oncogene-encoded proteins probably regulate other biological activities such as transmission of nerve impulses, phototransduction, chemotaxis, differentiation, etc. Alterations in pathways controlling such activities may play an important role in other diseases such as atherosclerosis and Alzheimer's disease. Hence, specific drugs designed to inhibit the activities regulated by mutant oncogene proteins may prove useful in the treatment not only of cancer, but of many other diseases as well.

When rat embryo fibroblasts undergo neoplastic transformation, microfilaments containing actins and myosins are reorganized from a bundle state into a randomly interwoven meshwork [Pollack et al., Proc. Natl. Acad. Sci. USA 72:994 (1975)]. This phenomenon, known as actin cable network diffusion, has been found to be a common characteristic of many such transformed cells. Studies indicate that changes in different cytoskeletal components are not an indirect consequence of transformation but are specific to the oncogenes that cause transformation [Franza et al., Cancer Cells 1:137 (1984); Leavit, J., in Human Fibroblast Transformation (Ed., G. Milo), CRC Press Inc., 1989, pp. 1–28].

Changes in the arrangement of cytoskeletal components have been associated with alterations in cell growth rate, attachment, saturation density and the expression of the differentiated phenotype. Such changes may favor neoplastic growth and play an important role in tumor initiation or progression. Although detailed understanding of the molecular mechanisms involved in these cytoskeletal changes is lacking, it is clear that some genes which are silent in normal cells are turned on in transformed cells, and that certain others that are expressed in normal cells are turned off following transformation.

Studies by Leavitt et al. [Nature 316:840 (1985)] and Garrels et al. [Cancer Cells 1:137 (1984)] have shown that smooth muscle α-actin isoform is expressed in both Rat2 and REF52 cells and is repressed following neoplastic transformation of the cells by several RNA and DNA tumor viruses.

Investigations on the human smooth muscle myosin light chain-2 (MLC-2) isoform have shown that the MLC-2 gene also is specifically repressed when fibroblasts undergo neoplastic transformation [Kumar et al., *Biochemistry* 28:4027 (1989); Kumar et al., in Cytoskeletal Proteins in Tumor Diagnosis, 1989, Weber et al., Eds., Cold Spring Harbor Press, p. 91]. Revertants of such transformed cells show normal levels of MLC-2 gene expression.

In view of the diverse roles played by oncogenes in cellular regulation and the relationship of oncogene activity to diseases such as cancer, it would be desirable to identify agents that can specifically alter oncogene-mediated biological processes, thereby reversing or suppressing the disease state. There is thus a need for specific in vitro screening systems for that purpose.

The proliferation and differentiation of mammalian cells are controlled by a family of polypeptide growth factors [Holley, *Nature* 258:487 (1975)]. All polypeptide growth factors act by binding to specific cell surface receptors that, upon activation, transduce a broad range of signals leading to cell growth and differentiation [James et al., *Ann. Rev. Biochem.* 53:259 (1984)]. A number of growth factors and their receptors have been characterized in recent years, including, e.g., epidermal growth factor (EGF), fibroblast growth factors (FGFs), platelet-derived growth factor (PDGF; a dimeric protein consisting of two "A" chains, two "B" chains or one "A" chain and one "B" chain), insulin-like growth factors (IGFs) and Bombesin. Many of the growth factor receptors have an intrinsic tyrosine kinase activity and contain very closely related structural elements.

Each growth factor may have a specificity for certain cells or tissue types. In many cases, however, they can also induce a response in other cell types. For example, EGF, the major target of which is epithelial cells, can also elicit a response from fibroblast cells. Fibroblast growth factor (FGF) is a potent stimulator of vascular endothelium and thus may be important in angiogenesis. At the same time FGF can stimulate other cell types such as fibroblasts and smooth muscle cells. PDGF is a key mitogen for smooth muscle cells and fibroblasts but has no direct effect on vascular endothelium or epithelium.

It has long been known that transformed cells in culture are generally able to grow in much lower concentrations of serum than are nontransformed cells. Serum is the normal source of growth factors for cultured cells. It was later discovered that fibroblasts transformed by certain retroviruses secrete factors which transiently induce normal cells to express a transformed phenotype [Todaro et al., in Genes and Proteins in Oncogenesis, 1983, Weinstein and Vogel, Eds. Academic Press., New York, N.Y., pp. 165–181; DeLarco et al., *Proc. Natl. Acad. Sci. USA* 75:4001 (1978); Todaro et al., *Cancer Res.* 38:4147 (1978)].

These factors, known as transforming growth factors (TGFs), consist of two functionally and structurally distinct groups of factors called TGF-α and TGF-β [Sporn et al., *Nature* 313:745 (1985)]. TGF-β acts as a growth inhibitor for certain cell types, and as a mitogen for other cell types. The discovery of these TGFs led to the suggestion that one of the ways by which cells become transformed is by endogenous production of growth factors for which they have receptors [Sporn et al., *N. Eng. J. Med.* 303:878 (1980)]. This internal production of growth factors is believed to serve as a constant stimulus for continued cell division, releasing the cells from their normal endogenous physiological controls.

The binding of growth factors to cellular receptors stimulates an array of biochemical responses, including changes in ion fluxes, activation of a number of protein kinases and alternation of transcriptional rates of several genes. These events culminate hours later in DNA replication and cell division. Recent studies have led to the delineation of pathways by which signals, generated at the membrane by the binding of a growth factor to its receptor, are transduced to the nucleus [Ullrich et al., *Cell* 61:203 (1990); Williams, *Science* 24:1564 (1989)]. Increased expression of genes encoding transcription factors is an important element of the signal transduction mechanism which assures long term transcriptional response of cells to growth factors.

Smooth muscle α-actin isoform is expressed in both vascular smooth muscle and fibroblast cells [Vandekerckhove et al., *Differentiation* 14:123 (1979); Leavitt et al., *Nature* 316:840 (1985)]. Actively proliferating aortic smooth muscle cells are known to contain relatively low levels of α-actin protein, whereas post-confluent cells show a nearly three-fold increase [Owens et al., *J. Cell Biol.* 102:343 (1988); Corjay et al., *J. Biol. Chem.* 264:10501 (1989)]. Addition of PDGF to quiescent aortic smooth muscle cells results in a decrease in the steady state level of α-actin mRNA (Corjay et al., supra).

Abnormal cell proliferation due to the action of various growth factors is associated with a number of diseases such as neoplasia, atherosclerosis and myelofibrosis. To alleviate these conditions, it would be desirable to identify agents that can antagonize the actions of the responsible growth factors.

One of the most direct approaches to the identification of growth factor antagonists has entailed the use of assays based upon the binding of radiolabeled ligands to cellular receptors. Such assay systems are quite laborious and time consuming, however, and determination of the specificity of a given antagonist requires the use of a number of different radiolabeled growth factors and membrane receptor preparations.

An even more serious drawback to such assays is that they can detect only antagonists which act at the receptor level and interfere with growth factor binding. As noted above, however, a complex sequence of events occurs after a growth factor binds to its receptor. Intervention at multiple points by appropriate antagonists may thus be possible, but antagonists acting at points other than at the receptor cannot be identified by radioligand/receptor assays.

There is therefore a need for a more broadly-based growth factor antagonist screen that could identify a much wider range of antagonists, regardless of their locus of action.

SUMMARY OF THE INVENTION

The present invention fills the above-mentioned needs by providing materials and methods for such screening.

More particularly, this invention provides methods for identifying antineoplastic agents comprising:

(a) providing a mammalian cell line containing:
  (i) a recombinant vector comprising a reporter gene operatively linked to a genetic control element responsive to oncogene-mediated neoplastic transformation, the rate of expression of which reporter gene is measurably altered when the cell line undergoes such neoplastic transformation, and
  (ii) an oncogene, the expression of which renders the cell line neoplastically transformed;

(b) contacting the neoplastically-transformed cell line of step (a) with a sample suspected to contain an antineoplastic agent; and (c) measuring the level of expression of the reporter gene, whereby an antineoplastic agent in the sample is identified by measurement of a level of expression of the reporter gene substantially similar to that of cells of the same cell line incubated in parallel which have been transformed by the vector of step (a)(i) but lack such oncogene and have not been exposed to the sample.

In some embodiments of the invention, the level of expression of the reporter gene is suppressed following neoplastic transformation. Antineoplastic agents reverse such suppression, causing an increased level of reporter gene expression. In other embodiments, the level of expression of the reporter gene is increased following neoplastic transformation. Antineoplastic agents cause a decreased level of reporter gene expression in such embodiments. In all of the embodiments, expression at the lower level is preferably negligible.

This invention further provides methods for identifying growth factor antagonists comprising:

(a) providing a mammalian cell line containing a recombinant vector comprising a reporter gene operatively linked to a genetic control element responsive to proliferation of the cell line, the rate of expression of which reporter gene is measurably decreased when the cell line is stimulated to proliferate by a growth factor;

(b) contacting the cell line of step (a) with a quantity of a growth factor sufficient to stimulate proliferation of the cell line and with a sample suspected to contain an antagonist of the growth factor; and (c) measuring the level of expression of the reporter gene, whereby an antagonist of the growth factor in the sample is identified by measurement of a substantially increased level of expression of the reporter gene, compared to the level measured in cells of the same cell line incubated in parallel with the growth factor but without the sample.

Preferably, the genetic control element used is a human MCL-2 isoform gene promoter or a human smooth muscle α-actin promoter, with the latter promoter being most preferred.

This invention still further provides recombinant vectors and host cells transformed by such vectors, for use in the methods of the invention.

BRIEF DESCRIPTION OF THE FIGURES

This invention can be more readily understood by reference to the accompanying figures, in which.

DESCRIPTION OF THE INVENTION

All references cited herein are hereby incorporated in their entirety by reference. All nucleic acid sequences disclosed follow the normal 5' to 3' convention, as read from left to right. Standard single-letter abbreviations are used for the nucleotide bases in the sequences (37 C.F.R. § 1.822).

As used herein, the term "reporter gene" is defined as either a DNA molecule isolated from genomic DNA, which may or may not contain introns, or a complementary DNA (cDNA) prepared using messenger RNA as a template. In either case, such DNA encodes an expression product that is readily measurable, e.g., by biological activity assay, enzyme-linked immunosorbent assay (ELISA) or radioimmunoassay (RIA).

The term "genetic control element" has two meanings herein. It means a DNA sequence (molecule) which, when operatively linked to a reporter gene in a host cell, is capable of responding to oncogene-mediated neoplastic transformation of the cell by either stimulating or suppressing expression of the linked reporter gene. It also means a DNA sequence which, when operatively linked to a reporter gene, causes a down regulation (i.e., reduction) in the level of expression of the reporter gene when a cell harboring the element is stimulated to multiply by a growth factor.

Figure 1:
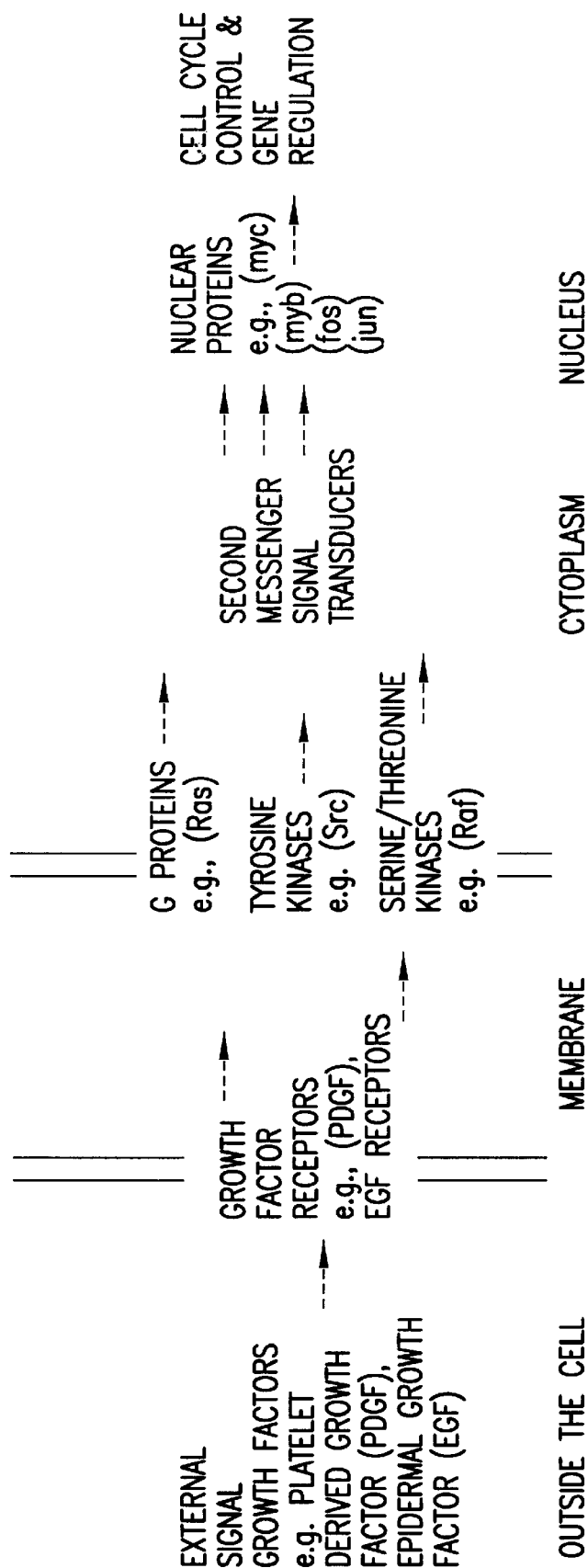
FIG. 1 is a schematic representation of some of the factors that are involved in the control of cell division.

The term "oncogene-mediated" refers to a process by which cells are neoplastically transformed by an oncogene, either directly or indirectly. Such transformation may involve unidentified intermediaries which are involved in the complex control of cell division (see FIG. 1) and may be initiated directly by expression of an oncogene within a cell, or indirectly in a process by which another neoplastic agent such as a chemical carcinogen or radiation causes expression of an otherwise latent oncogene within a cell.

As used in this invention, the term "neoplastic transformation" is defined as a process by which a normal cell obtains an altered phenotype characterized by:

(a) morphological change (normally flat cells become rounded and actin cable network diffusion occurs);

(b) loss of contact inhibition (cells pile up and become multi-layered in tissue culture);

(c) anchorage independence (cells can grow in soft agar without substrate contact); and (d) tumorigenicity (cells injected into immune-deficient animals produce tumors).

An "antineoplastic agent" is defined as a chemical compound that can substantially reverse or suppress oncogene-mediated neoplastic transformation as defined herein, thereby restoring the normal cell phenotype. This restoration of the normal cell phenotype is accompanied by a concomitant alteration in the rate of reporter gene expression measured in the methods of this invention.

A "normal" cell in the context of this invention is a cell that does not manifest the above-mentioned phenotypic characteristics but which may or may not exhibit an altered karyotype and an indefinite lifespan in tissue culture (i.e., normal cells may be cells of an established cell line).

The term "α-actin promoter" means a particular genetic control element which has a nucleotide sequence corresponding to the sequence of bases of a region of the human smooth muscle α-actin gene. Parts of the human smooth muscle α-actin gene relevant to the present invention have been disclosed by Reddy et al. [*J. Biol. Chem.* 265:1683 (1990)] and by Ueyama et al. [*Mol. Cell. Biol.* 4:1073 (1984)].

Cells which have been "stably transformed" have recombinant DNA incorporated into their genomic DNA. Such stably incorporated DNA is retained by the transformed cells because it is introduced into the cells with a selection marker which forces retention when the cells are grown in a selection medium. The present invention preferably employs mammalian cell lines that have been stably transformed.

In some embodiments of the invention, which can be used to screen for antineoplastic agents, the vectors contain reporter genes operatively linked to genetic control elements that are responsive to oncogene-mediated neoplastic transformation. Genetic control elements that can be used in these embodiments include all DNA sequences which, when operatively linked to a reporter gene in a host cell, are capable of responding to oncogene-mediated neoplastic transformation of the cell by either stimulating or suppressing expression of the linked reporter gene. Especially preferred are promoters and enhancers meeting such functional requirements.

One genetic control element that can be used to screen for antineoplastic agents is a murine VL30 transcriptional element. Owen et al. [*Mol. Cell. Biol.* 10:1 (1990)] have shown in transient expression assays that expression of a firefly luciferase gene operatively linked to a VL30 long-terminal repeat/mouse major β-globin promoter construct is increased in mouse NIH 3T3 cells harboring the construct, following neoplastic transformation of the cells by the human Ha-c-ras EJ bladder carcinoma gene. Another element that can be used which responds to oncogene-medicated neoplastic transformation by increasing expression of a linked gene is the ras-responsive human β-polymerase promoter described by Kedar et al. [*Mol. Cell. Biol.* 10:3852 (1990)].

Other genetic control elements that can be used to screen for antineoplastic agents, in contrast to the foregoing elements, respond to oncogene-mediated neoplastic transformation by suppressing expression of genes to which they are operatively linked. Such elements, which include, e.g., the promoter regions of the rat thyroglobulin gene [Avvedimento et al., *Proc. Natl. Acad. Sci. USA* 85:1744 (1988)], the major histocompatibility (MCH) class I gene [Ackrill et al., *Oncogene* 3:483 (1988)], the human smooth muscle α-actin isoform gene [Leavitt et al., *Nature* 316:840 (1985); Garrels et al. *Cancer Cells* 1:137 (1984)] and the human smooth muscle myosin light chain-2 (MLC-2) isoform gene [Kumar et al., *Biochemistry* 28:4027 (1989); Kumar et al., in Cytoskeletal Proteins in Tumor Diagnosis, 1989, Weber et al., Eds., Cold Spring Harbor Press, p. 91].

Although the above-mentioned elements are promoter sequences, transcriptional enhancer sequences can be used as well. Enhancers are genetic elements that can influence the level of expression of genes with which they are associated. Unlike promoters, which must be positioned upstream (i.e., in the 5' direction) of the genes they control, enhancers may be either upstream or downstream.

One enhancer that can be used in this invention is the polyoma virus enhancer described by Imler et al. [*Nature* 332:275 (1988)], which mediates Ha-ras activation in mouse myeloma and fibroblast cells. Another has been located within promoter sequences of the MHC class I gene. Lenardo et al. [*EMBO J.* 8:3351 (1989)] have demonstrated that N-myc oncogene expression in a rat neuroblastoma cell line leads to reduced binding of a transcription factor that activates this enhancer. The result is suppression of MCH class I gene expression.

Genetic control elements preferred for use in screening for antineoplastic agents produce suppression of reporter gene expression following oncogene-mediated neoplastic transformation. Such elements are preferred because they are unlikely to yield false positive results with agents that are merely cytotoxic, instead of specific for oncogene-mediated processes. Toxic substances will cause general metabolic damage in the host cells and will not produce an elevation of gene expression. Especially preferred are the promoter regions of the human MLC-2 isoform gene and the human smooth muscle α-actin isoform gene, the latter of which is used to illustrate the invention in the Example below.

In other embodiments of the invention, which can be used to screen for growth factor antagonists, the vectors contain reporter genes operatively linked to genetic control elements that are responsive to stimulation of proliferation of the cell lines by growth factors. Genetic control elements that can be used for this purpose include any DNA sequence which, when operatively linked to a reporter gene in a host cell, are capable of responding to growth factor-stimulated proliferation of the cells by down regulation of the level of expression of the linked reporter gene. Especially preferred are promoters meeting such functional requirements.

Surprisingly, it has been found that the promoters of the human smooth muscle MLC-2 isoform gene and the human smooth muscle α-actin gene can be used to screen for both antineoplastic agents and growth factor antagonists. For that reason, these promoters are preferred for use in this invention.

Especially preferred is the region of the human smooth muscle α-actin gene which begins at the 5' (upstream) end with nucleotide residue −896 and extends in the 3' (downstream) direction to encompass the remainder of the 5' flanking region, exon 1, intron 1, and the 5' noncoding sequences from exon 2. Residue −896 is numbered relative to the first base of the transcription initiation site of the gene, with that base being designated +1.

Figure 3:
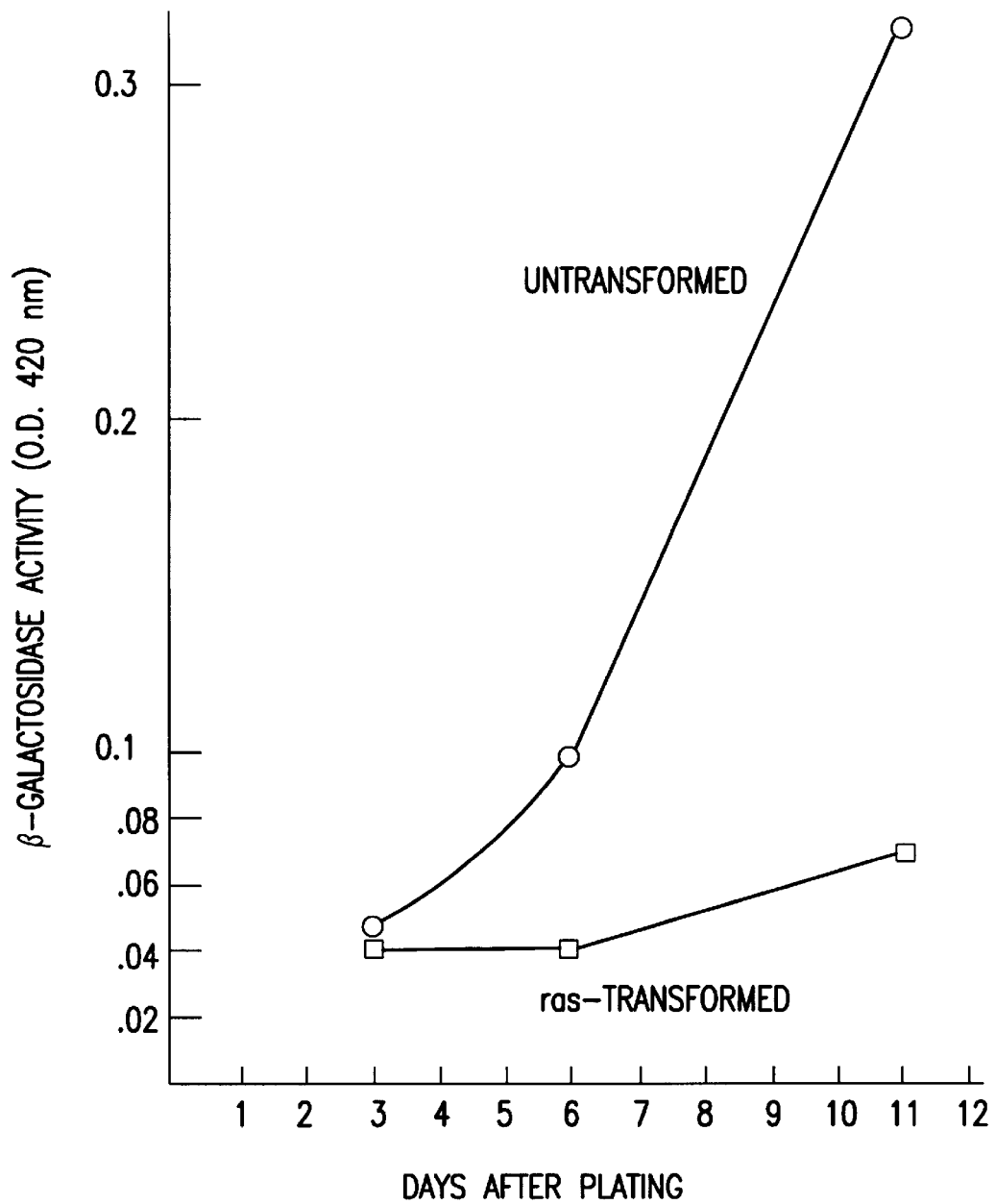
FIG. 3 is a graphical representation of the results of an assay for β-galactosidase activity in Rat-6 cells that were stably transformed with plasmid pαAP126 and either neoplastically transformed with plasmid pH06T1 (ras-transformed) or not (Untransformed). β-Galactosidase activity (O.D. at 420 nm) is shown as a function of time after cell plating.

The sequence of much of the involved region of the gene is defined in the Sequence Listing by SEQ ID NO:1, wherein bases 1 to 1127 correspond to bases −896 to +232 of the sequence of FIG. 3 of Reddy et al., supra. The guanosine residue at position 896 of SEQ ID NO:1 corresponds to the first base of the transcription initiation point of the human smooth muscle α-actin gene (i.e., +1). Bases 1–6 and 902–910 of the sequence defined by SEQ ID NO:1 define an EcoRI and DraIII restriction site, respectively, which are used below to make an illustrative embodiment of the invention.

Figure 2:
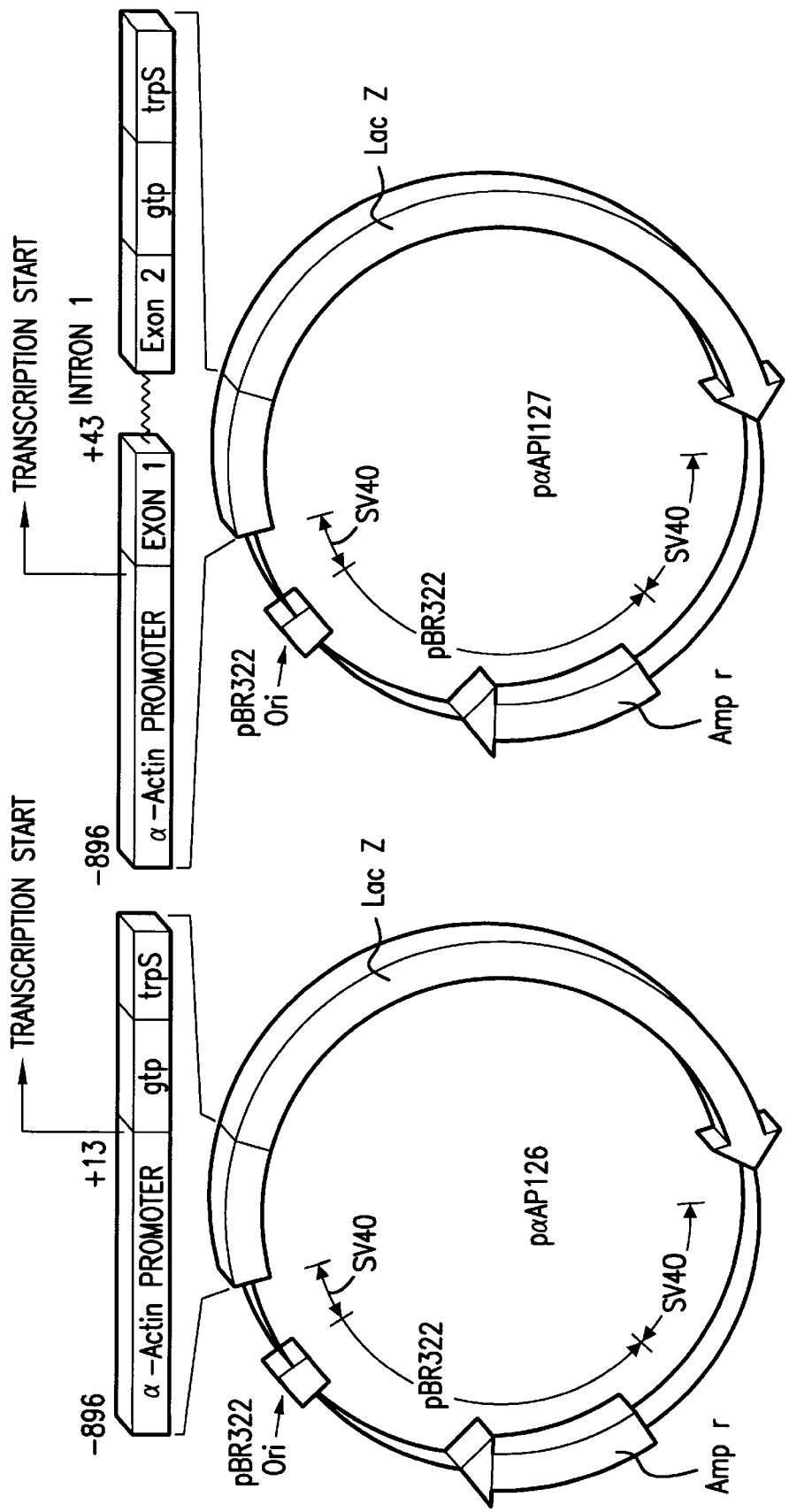
FIG. 2 is a schematic representation of plasmids pαAP126 and pαAPI127.

Other relevant regions of the human smooth muscle α-actin gene that can be employed in this invention are disclosed by Ueyama et al., supra, which provides in FIG. 2 a restriction map covering, inter alia, exons 1 and 2 and intron 1 of the human smooth muscle α-actin gene.

All present embodiments of the genetic control elements based upon the human smooth muscle α-actin gene comprise DNA having a nucleotide sequence corresponding to the sequence of about base 1 to about base 910 of the sequence defined by SEQ ID NO:1. Other embodiments are longer in the 3' direction, containing one or more additional bases having a sequence corresponding to the sequence of bases 911 to 1127 of the sequence defined by SEQ ID NO:1. Still other embodiments contain additional bases comprising all or part of intron 1 and/or exon 2, up to but not including the translational start signal of exon 2.

Those skilled in the art can readily make such embodiments using the sequence information in SEQ ID NO:1 and the known restriction map of the human smooth muscle α-actin gene (Ueyama et al., supra). By the application of standard sequencing methods, the complete nucleotide sequence of intron 1 can also be determined, thereby permitting the construction of embodiments not terminated by a known (or determinable) restriction cleavage point, if desired.

In particluarly preferred exemplary embodiments described in the Example below, the genetic control element of one plasmid, pαAP126, has a nucleotide sequence corresponding to the sequence of bases 1 to 910 of SEQ ID NO:1. The genetic control element of another plasmid, pαAPI127, has a nucleotide sequence corresponding to all of the sequence defined by SEQ ID NO:1 and, in addition, contains intron 1 (~1.5 kb) and the first (5') 13 base pairs of exon 2 of the human smooth muscle α-actin gene. Deletion of part of intron 1 was accomplished by restriction endonuclease cleavage and ligation of a 54 bp double-stranded oligodeoxyribonucleotide linker, the sequence of which is defined by SEQ ID NO: 2. In both of these exemplary plasmids, the genetic control elements are operatively linked to E. coli LacZ coding sequences (encoding β-galactosidase).

Plasmids pαAP126 and pαAPI127 can be used both to screen antineoplastic agents and to screen growth factor antagonists.

The genetic control elements of the invention can be prepared by standard methods based upon the known sequences of the genes. For example, they can be chemically synthesized using the phosphoramidite solid support method of Matteucci et al. [J. Am. Chem. Soc. 103:3185 (1981)], the method of Yoo et al. [J. Biol. Chem. 764:17078 (1989)], or other well known methods. Alternatively, since the sequences of the elements and the site specificities of the many available restriction endonucleases are known, one skilled in the art can readily identify and isolate the elements from genomic DNA and cleave the DNA to obtain a desired sequence. The PCR method [Saiki et al., Science 239:487 (1988)] can also be used to obtain the same result. Primers used for PCR can also be designed to introduce appropriate new restriction sites, to facilitate incorporation into a given vector.

Isolation of the human smooth muscle α-actin promoter from a cosmid library constructed using human placenta DNA has been described in detail by Reddy et al [J. Biol. Chem. 265:1683 (1990)]. The same approach taken by Reddy et al. can be used to isolate other promoter sequences.

In the Example below, the human smooth muscle α-actin promoter used in the construction of exemplary plasmid pαAP126 was obtained by restriction endonuclease cleavage of plasmid pα (Reddy et al., supra). The promoter could as easily have been obtained, however, by the use of the polymerase chain reaction (PCR) method [Saiki et al., Science 239:487 (1988)].

To generate DNA containing the human smooth muscle α-actin promoter as present in plasmid pαAP126, two oligodeoxynucleotides having nucleic acid sequences defined by SEQ ID NO:3 and SEQ ID NO:4 are synthesized and used as primers for PCR using human genomic DNA (Clontech Laboratories, Inc., Palo Alto, Calif.) as template. The resulting DNA fragment is blunt-ended by enzymatically filling in the overhangs, and the fragment is ligated to prepared plasmid pCH126 as described below to produce plasmid pαAP126.

Insertion of a genetic control element into a vector is easily accomplished when the termini of both the element and the vector comprise the same restriction site. If this is not the case, it may be necessary to modify the termini of the element and/or vector by digesting back single-stranded DNA overhangs generated by restriction endonuclease cleavage to produce blunt ends, or to achieve the same result by filling in the single-stranded termini with an appropriate DNA polymerase. Alternatively, any site desired may be produced by ligating nucleotide sequences (linkers) onto the termini. Such linkers may comprise specific oligonucleotide sequences that define desired restriction sites. The cleaved vector and the control elements may also be modified if required by homopolymeric tailing.

Any of the well-known reporter genes can be operatively linked to one of the foregoing elements. Examples of suitable reporter genes include but are not limited to E. coli β-galactosidase [An et al., Mol. Cell. Biol. 2:1628 (1982)], xanthine-guanine phosphoribosyl transferase [Chu et al., Nucleic Acids Res. 13:2921 (1985)], galactokinase [Shumperli et al., Proc. Natl. Acad. Sci. USA 79:257 (1982)], interleukin-2 [Cullen, Cell 46:973 (1986)], thymidine kinase [Searle et al., Mol. Cell. Biol. 5:1480 (1985)], firefly luciferase [De Wet et al., Mol. Cell. Biol. 7:725 (1987)], alkaline phosphatase [Henthorn et al., Proc. Natl. Acad. Sci. USA 85:6342 (1988)], secreted placental alkaline phosphatase [Berger et al., Gene 66:1 (1988)] and chloramphenicol acetyltransferase (CAT) [Gorman et al., Mol. Cell. Biol. 2:1044 (1982); Tsang et al., Proc. Natl. Acad. Sci. USA 85:8598 (1988)]. Many of these and other useful reporter genes are available from commercial sources.

Expression products of the reporter genes can be measured using standard methods. For example, bioassays can be carried out for biologically active proteins such as interleukin-2. Enzyme assays can be performed when the reporter gene product is an enzyme such as alkaline phosphatase or β-galactosidase. Alternatively, various types of immunoassays such as competitive immunoassays, direct immunoassays and indirect immunoassays may be used.

Such immunoassays involve the formation of immune complexes containing the reporter gene product and a measurable label. As used herein, the term "label" includes moieties that can be detected directly, such as fluorochromes and radiolabels, and moieties such as enzymes that must be reacted or derivatized to be detected.

In competitive immunoassays, samples from induced cultures (following cell disruption if the reporter gene product is not secreted) are incubated with an antibody against the reporter gene product and a known amount of labeled reporter gene product. Any unlabeled product produced by the cells competes with the labeled material for binding to the antibody. The resulting immune complexes are separated and the amount of labeled complex is determined. The reporter gene product produced by the cells can be quantified by comparing observed measurements to results obtained from standard curves.

Direct immunoassays involve incubating culture samples with a labeled antibody against the reporter gene product and separating any immune complexes that form. The amount of label in the complexes is determined and can be quantified by comparison to standard curves.

Enzyme-linked immunosorbant assays (ELISAs) can also be carried out by well known methods, e.g., as described in U.S. Pat. No. 4,665,018 to Vold.

The particular label used will depend upon the type of immunoassay used. Examples of labels that can be used include, e.g., radiolabels such as $^{32}P$, $^{125}I$, $^{3}H$ and $^{14}C$; fluorescent labels such as fluorescein and its derivatives, rhodamine and its derivatives, dansyl and umbelliferone;

chemiluminescers such as the various luciferin compounds; and enzymes such as horseradish peroxidase, alkaline phosphatase, lysozyme and glucose-6-phosphate dehydrogenase.

The antibody or reporter gene product, as the case may be, can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels.

The genetic control elements used in this invention can be inserted into many reporter gene-containing vectors, including but not limited to plasmids pSV2Apap, pMAMneo-CAT, pMAMneo-LUC, pSVOCAT, pBCO, pBLCAT2, pBLCAT3, pON1, pCH110, pCH126 and various plasmids described by De Wet et al., supra. Where a desired vector contains a different promoter, the promoter can be excised using standard methods and replaced by a promoter that is responsive to oncogene-mediated neoplastic transformation. In the Example below, the SV-40 promoter in plasmid pCH110 was excised and replaced with the human smooth muscle α-actin promoter.

As used herein, the term "recombinant vector" includes both recombinant plasmids such as those mentioned above and recombinant retroviral vectors, which can also be engineered as described by Geller et al. [*Proc. Natl. Acad. Sci. USA* 87:1149 (1990)] to contain a genetic control element operatively linked to a reporter gene.

The foregoing recombinant vectors can be used to transform any cell that is normal but capable of becoming neoplastically transformed, as herein defined. Cells from fish, amphibian or avian sources could be used as long as they meet the foregoing requirements, but mammalian cells are preferred. Although cells from fresh tissue explants (primary cells) could in principle be used, the use of established cell lines is preferred. Many such cell lines are available including, e.g., the Rat-2 (ATCC CRL 1764), Rat-6, NIH 3T3 mouse (ATCC CRL 1658), FRTL Fischer rat thyroid (ATCC CRL 1468) and L-M (TK–) mouse (ATCC CCL 1.3) cell lines.

The choice of a cell or cell line for use in screening antineoplastic agents will be dictated by the known or determinable specificities of the genetic control element and oncogene used. For example, the MHC class I promoter can be used in conjunction with the Ad 12 E1A oncogene in primary baby rat kidney cells [Ackrill et al., *Oncogene* 3:483 (1988)]. The polyoma virus transcriptional enhancer/ras oncogene can be used in mouse L-M (TK–) cells. The human smooth muscle α-actin promoter/ras oncogene can be used in Rat-2, Rat-6 or other cells which normally express α-actin. The rat thyroglobulin promoter/TL src or TL mos oncogenes can be used in FRTL rat thyroid cells. NIH 3T3 cells can be used with the human β-polymerase promoter, in conjunction with the ras oncogene.

Although cells for use in the present invention could be transiently transformed, the use of stably-transformed cells is preferred. Stable transformation of a mammalian cell line can be accomplished by using standard methods to co-transfect the cells with one of the above-mentioned recombinant vectors and with a second vector which confers resistance to a selection agent such as an antibiotic. Alternatively, transformation can be carried out with a single vector containing both the genetic control element/reporter gene component and the selection marker gene. Recombinant retroviral vectors can also contain a selection marker gene to produce stable transformation. In the Example below, co-transfection was carried out using plasmids pIBW and pMAMneo, which provide a dominant selectable marker for resistance to antibiotic G418 (neomycin) in mammalian cells. Other well known plasmids such as pSV2neo can be used for the same purpose.

Neoplastic transformation of cells which have been stably transformed by a genetic control element/reporter gene construct is most conveniently carried out by further transformation of the cells with an expression vector containing a desired oncogene such as the src, neu, sis, raf, abl, N-ras, Ki-ras or Ha-ras oncogene. These oncogenes are well known in the art and in use in laboratories around the world. Most are also available for purchase from commercial sources or from the American Type Culture Collection NIH Repository of Human and Mouse DNA Probes and Libraries. They can be obtained already incorporated into a vector suitable for cell transformation or they can be excised from the vectors in which they are provided and inserted into another vector, using standard methods.

Insertion of oncogenes into cells via recombinant vectors is most convenient, although expression of latent oncogens can be induced in the host cells instead by the use of an agent such as radiation (preferably X-radiation) or a chemical carcinogen. For example, Rhim et al [*Carcinogenesis* 8:1165 (1987)] have shown that a latent H-ras oncogene is activated following transformation of certain human fibroblasts by 3-methylcholanthrene.

Oncogenes can also be introduced into the cells using viral vectors carrying the genes. Examples of such viral vectors include, e.g., retroviral vectors described by Dotto et al. [*Nature* 318:472 (1988)].

In screening antineoplastic agents using the methods of the invention, the level of reporter gene expression is first preferably measured in cells which have been transformed with a genetic control element/reporter gene construct but are not neoplastically transformed. The cells are then neoplastically transformed, contacted with serial dilutions of a sample suspected to contain an antineoplastic agent (e.g., a solution in which a compound has been dissolved or a fraction or pool from a chromatography column or another purification method) or control buffer, and following a period of incubation to allow such agent to affect expression of the reporter gene, the level of expression of the reporter gene is measured. An antineoplastic agent in the sample is identified by measurement of a level of reporter gene expression substantially similar to that of the cell line prior to neoplastic transformation.

In cases where the genetic control element used causes an increased level of reporter gene expression following neoplastic transformation (e.g., the ras-responsive murine VL30 transcriptional and human β-polymerase promoter elements), controls are preferably run in parallel using the same type of cells transformed with the same reporter gene operatively linked to a promoter that is not responsive to neoplastic transformation. Antineoplastic agents that are specific antagonists of oncogene-mediated neoplastic transformation and are not merely generally cytotoxic will cause reduced reporter gene expression in cells harboring the oncogene-responsive element only.

The choice of cells or cell lines for use in screening growth factor antagonists will be dictated by the known or determinable specificities of the genetic control element and growth factor(s) used. For example, the human smooth muscle α-actin promoter can be used to screen for antagonists of a variety of growth factors in Rat-2, Rat-6 or other cells which normally express α-actin. Growth factors that can be used in this system include but are not limited to TGF-α and -β; PDGF-AA, -BB or -AB; EGF (epidermal growth factor); bFGF (basic fibroblast growth factor), insulin-like growth factors and Bombesin. Preferably, the cells will be stably transformed as described above.

In screening growth factor antagonists using the methods of the invention, cells are provided which are transformed with one of the recombinant vectors of the invention. The cells are plated in a culture medium appropriate to the kind of cells used. Because mammalian or avian cells are typically passaged and plated in medium containing serum, the cultures are preferably incubated for a period of at least several days prior to beginning the assay, to permit the cells to deplete the medium of serum growth factors and to thereby become quiescent.

The cells are then stimulated to proliferate by addition to the culture medium of none (control) or varying quantities of a growth factor(s) to which the cells are responsive and for which an antagonist is sought. Parallel cultures containing the varying growth factor quantities are also treated with samples suspected to contain antagonists of the growth factors. These samples can be aqueous or water-miscible solutions in which isolated compounds have been dissolved, or individual or pooled fractions from purification steps such as chromatographic or electrophoretic fractions.

If desired, the growth factors can be dissolved in a physiologically compatible solvent such as dimethyl sulfoxide (DMSO) prior to aliquoting in the culture medium. Carrier proteins such as bovine or human serum albumin may be added to the medium to prevent adsorptive loss of low-level quantities of growth factors on test tubes used to make dilutions, pipettes and/or culture vessels.

All of the cultures are then incubated together under conditions in which the growth factors, in the absence of an antagonist, will stimulate proliferation of the cells. Typical incubations are carried out at 37° C. in a humidified $CO_2$ incubator, although the choice of conditions will be apparent to those skilled in the art and will depend, e.g., upon the nature of the cells, the medium used and the type of culture container.

Incubation is continued for a period of time to permit development of a strong proliferative response, at which time the level of expression of the reporter gene is measured by an appropriate assay. The optimal time for making the measurement after growth factor addition is determined by routine experimentation but will typically be in the range of about 24 to 72 hours for mammalian or avian cells, preferably 48 hours.

The highest levels of reporter gene expression will be measured in the control (growth factor-free) cultures. Where a culture contains a growth factor alone, a reduction in the level of reporter gene expression will be measured, the degree of which will be a direct function of the quantity of growth factor added to the medium. Growth factor antagonists present in the samples added to some of the cultures will be identified by measuring a substantially increased level of reporter gene expression, compared to the level measured in the parallel cultures containing growth factor alone.

A substantially increased level of reporter gene expression is defined as an increase of at least about 5%, preferably about 50% and more preferably about 90–100% of the level measured in the complete absence of growth factor. Of course, the degree of increase may be influenced by the quantity of antagonist present in the sample compared to the quantity of growth factor used and the efficiency of the antagonist.

EXAMPLE

The present invention can be illustrated by the following, non-limiting Example. Unless otherwise specified, percentages given below for solids in solid mixtures, liquids in liquids, and solids in liquids are on a wt/wt, vol/vol and wt/vol basis, respectively. Sterile conditions were maintained during cell culture.

General Methods and Reagents

Unless otherwise noted, standard recombinant DNA methods were carried out essentially as described by Maniatis et al., Molecular Cloning: A Laboratory Manual, 1982, Cold Spring Harbor Laboratory.

Small scale isolation of plasmid DNA from saturated overnight cultures was carried out according to the procedure of Birnboim et al. [*Nuc. Acids Res.* 7:1513 (1979)]. This procedure allows the isolation of a small quantity of DNA from a bacterial culture for analytical purposes. Unless otherwise indicated, larger quantities of plasmid DNA were prepared as described by Clewell et al. [*J. Bacteriol.* 110:1135 (1972)].

Specific restriction enzyme fragments derived by the cleavage of plasmid DNA were isolated by preparative electrophoresis in agarose followed by electroelution (Maniatis et al., supra, p. 164). Gels measuring 9×5 ½ cm were run at 50 mA for 1 hour in Tris-Acetate buffer (Maniatis et al., supra, p. 454) and then stained with 1 mg/ml ethidium bromide to visualize the DNA. Appropriate gel sections were excised and melted at 65° C. for 10 minutes and then diluted with 5 ml of a low salt buffer containing 0.2M NaCl, 20 mM Tris-HCl (pH 7.4) and 1 mM EDTA. The DNA was then concentrated using a Elutip-D column (Schleicher and Schuell Inc., Keene, N.H.) following the manufacturer's instructions and precipitated at −20° C. with ethanol in the presence of 10 mg of yeast tRNA carrier (Bethesda Research Laboratories, Bethesda, Md.).

The restriction enzymes, DNA polymerase I (Klenow fragment) and T4 DNA ligase were products of New England Biolabs, Beverly, Mass., and the methods and conditions for the use of these enzymes were essentially those of the manufacturer. T4 DNA ligation was carried out for 16 hours at 4° C. in a buffer containing 50 mM Tris-HCl, pH 7.8, 10 mM $MgCl_2$, 20 mM dithiothreitol, 1 mM ATP and 50 mg/ml bovine serum albumin. Klenow blunt-ending of single-stranded DNA ends was carried out in restriction enzyme buffer which had been adjusted to contain 1 mM dGTP, dATP, dCTP and TTP.

Plasmids pIBW and pCH110 are available from Pharmacia LKB Biotechnology, Inc., Piscataway, N.J. Plasmid pMAMneo was obtained from Clontech Laboratories, Inc., Palo Alto, Calif. Plasmid pH06T1 [Spandidos et al., *Nature* 310:469 (1984)] comprising the Harvey ras (Ha-ras) oncogene was used to neoplastically transform Rat-2 and Rat-6 cells, both of which are normal rat cell lines deficient in nuclear thymidine kinase.

Plasmid pH06T1 is functionally equivalent to plasmid pHB-11 (ATCC 41013), which also contains the Ha-ras oncogene and can be used with equal efficacy to neoplastically transform such cells. One of the known viral vectors carrying the ras oncogene could also be used instead of pH06T1 to carry the gene into the cells.

Growth factors were purchased from Collaborative Research (Beverly, Mass.). Chlorophenol-red-β-galactopyrannoside (CPRG) was purchased from Boeringer-Mannheim Chemicals (Indianapolis, Ind.), while 5-Bromo-6-chloro-3-indolyl-β-galactopyrannoside (X-gal) was obtained from Sigma Chemicals (St. Louis, Mo.). Goat antibodies against human PDGF and goat anti-human IgG are available commercially.

Both Rat-2 and Rat-6 cells are sublines of the Rat-1 line described by Topp [*Virology* 113:408 (1981)]. Both are functionally equivalent and have produced similar data using the constructs and methods described below. Rat-2 cells were obtained from the American Type Culture Collection, Rockville, Md. (accession No. ATCC CRL 1764).

Synthetic oligonucleotide primers having nucleic acid sequences as defined in the Sequence Listing by SEQ ID NO:3 and SEQ ID NO:4 can be synthesized by standard methods.

Cell Culture

Rat-2 and Rat-6 cells were grown in Dulbecco's Modified Eagle's Medium (DMEM) supplemented with 10% heat-inactivated fetal calf serum (FCS), 2 mM glutamine and 100 gg/ml gentamycin. Both cell lines were maintained in a humidified incubator with 5% $CO_2$ at 37° C. The media and cell culture reagents were purchased from Hazleton Biologics, Inc., Lenexa, Kans. Stock cultures containing about $5 \times 10^6$ cells per 100 mm dish were routinely split 1:5 or 1:6 by trypsinization and replating every 3 or 4 days.

Transfection

Plasmids were transfected into $5 \times 10^5$ Rat-2 or Rat-6 cells in 100 mm culture dishes (Becton Dickinson & Co., Lincoln Park, N.J.), essentially as described by Graham et al. [*Virology* 52:456 (1973)]. Co-transformation with pIBW or pMAMneo and pαAP126 or pαAPI127was carried out at a ratio of 1:10 (pIBW or pMAMneo:pαAP126 or pαAPI127). Stably-transformed cells were selected in a medium consisting of the above-mentioned medium supplemented with 200 μg/ml G418 (Sigma Chemical Co., St. Louis, Mo.). After two weeks of incubation in selection medium (replaced every 3 days), individual G418-resistant (neomycin-resistant) colonies were picked by the agar-overlay method (Reid, L. C., in Methods in Enzymology, Vol. LVIII, 1979, Jakoby et al., Eds., Academic Press, New York, N.Y.) and expanded into mass culture.

β-Galactosidase Assays

β-Galactosidase activity in cultured clones was detected by the X-gal method, essentially as described by An et al. [*Mol. Cell. Biol.* 2:1628 (1982)]. Briefly, duplicate sets of stably-transformed Rat-2 or Rat-6 colonies containing about $10^5$ cells/well were incubated in 24-well tissue culture plates (Becton Dickinson) in 1-ml volumes of DMEM for 4 days at 37° C. The cells in each well were then fixed for 15 minutes in 1-ml volumes of a solution containing 1% glutaraldehyde, 0.1M sodium phosphate buffer (pH 7.0) and 1 mM $MgCl_2$ and then incubated for 4 hours at 37° C. with a solution containing 0.2% X-gal (5-bromo-4-chloro-3-indolyl-β-galactopyranoside; Sigma Chemical Co., St. Louis, Mo.), 10 mM sodium phosphate (pH 7.0), 150 mM NaCl, 1 mM $MgCl_2$, 3.3 mM $K_4Fe(CN)_6.3H_2O$ and 3.3 mM $K_3Fe(CN)_6$. Following the incubation, the X-gal solution was removed and 10% glycerol was added to the wells. Positive colonies showed blue color which was stable in 10% glycerol solution.

Quantitative β-galactosidase assays were carried out on Rat-2 or Rat-6 transformants essentially as described by Miller [Experiments in Molecular Genetics, 1972, Cold Spring Harbor Laboratory Press, Cold Spring Harbor, N.Y.], except that although o-Nitrophenyl β-D-galactoside (ONPG) was used as the substrate for antineoplastic agent screening, chlorophenol-red-β-galactopyrannoside (CPRG) was used instead for growth factor antagonist screening. Briefly, about $1 \times 10^4$ cells were seeded in 0.1 ml of DMEM into the wells of a 96-well microtiter plate (Becton Dickinson) and incubated at 37° C. At various times thereafter, the medium was removed and the cells were rinsed with phosphate buffered saline.

The cells were lysed for 20 minutes at 4° C. with 0.05-ml aliquots of a 50 mM sodium phosphate solution (pH 7.0) containing 5 mM β-mercaptoethanol and 0.5% Nonidet P-40 (octylphenol-ethylene oxide) detergent. After lysing the cells, 50 μl of LacZ reaction buffer containing 800 μg/ml ONPG in 50 mM sodium phosphate buffer (pH 7.0), 10 mM potassium chloride, 1 mM $MgSO_4$ and 50 mM β-mercaptoethanol were added to each well. The plates were incubated for 4 hours at 37° C., after which the reaction was terminated by the addition of 30 μl of a freshly-prepared solution of 1M $Na_2CO_3$. The absorbance of the solutions in the wells was measured at 420 (ONPG) or 590 (CPRG) nm.

Construction of Plasmid phαAP126

To produce an exemplary genetic control element/reporter gene construct, plasmid pCH110 containing the *E. coil* lacZ gene under the control of the SV-40 early promoter) was prepared by excising the SV-40 promoter by digesting the plasmid with PvuII/HindIII. The cleaved plasmid was then blunt-ended by filling the HindIII overhangs with T4 DNA polymerase and ligated to form plasmid pCH126, which contained a unique HindIII site 5' of the lacZ gene. Plasmid pCH126 was then cleaved at the HindIII site.

The human smooth muscle α-actin promoter was excised from plasmid pα [Reddy at al., *J. Biol. Chem.* 265:1683 (1990)] by cleaving the plasmid with EcoRI/DraIII. Following gel purification, an about 840 bp DNA fragment containing the promoter was blunt-ended by enzymatic overhang filling and then ligated to the HindIII-digested plasmid pCH126 at 15° C. for 22 hours in a ligation mixture consisting of 50 mM Tris-HCl (pH7.5), 10 mM $MgCl_2$, 1 mM ATP and 10 units of T4 DNA ligase.

The ligation mixture was introduced into competent *E. Coli* strain DH5α cells (Bethesda Research Labs, Gaithersburg, Md.) using the $CaCl_2$ transformation procedure (Maniatis et al., supra, page 250). Using nucleotide sequence information disclosed by Reddy et al., supra, transformant clones bearing the human smooth muscle α-actin promoter in the correct orientation were identified by restriction digestion of partially-purified plasmid DNA with EcoRI and PstI. This digestion produced five restriction fragments of 206, 752, 995, 2300 and 3400 bp from plasmids having the correct promoter orientation. Further analytical confirmation of the correct plasmid was obtained by digestion with ApaI and PstI, which produced expected restriction fragments of 270, 958, 2182 and 4232 bp. The plasmid thus identified was designated pαAP126 (FIG. 2).

Construction of Plasmid pαAPI127

A 1.8 kb BamHI/EcoRI fragment containing the second exon of the human smooth muscle α-actin gene was isolated from a cosmid library constructed in C2BX using human placental DNA (Reddy et al., supra). This fragment was then cloned into plasmid pAT153 (Maniatis et al., supra, page 6) which had been prepared by cleavage with the same enzymes to produce a first intermediate construct. This intermediate was digested with PvuII and EcoRI, gel purified and ligated with a 54 bp double-stranded oligodeoxyribonucleotide having a 5' to 3' nucleotide sequence defined by SEQ ID NO:2. The 3' to 5' strand of this double-stranded oligodeoxyribonucleotide was complementary to the 5' to 3' strand except for a four-base (TTAA) extension at the 5' end, which created an EcoRI site when the strands were annealed together. Both strands were chemically synthesized using standard methods.

Ligation of the double-stranded oligodeoxyribonucleotide produced a second intermediate construct containing intron 1 sequences and exon 2 sequences immediately upstream of the translation initiation ATG codon. The second intermediate plasmid was digested with BamHI and then ligated with an EcoRI/BamHI fragment containing the promoter and first exon of the human smooth muscle α-actin gene, to produce a plasmid designated pAI-AT153.

Plasmid pAI-AT153 was digested with EcoRI to produce a 3.5 kb restriction fragment that was isolated, blunt ended and then ligated into HindIII-cleaved, blunt-ended plasmid pCH126. The result was plasmid pαAPI127, which is shown schematically in FIG. 2. The plasmid containing the promoter in the correct orientation was identified by restriction cleavage and gel analysis. Upon digestion with BamHI, the correct plasmid yielded two bands 4.5 and 7.0 kb in size.

Antineoplastic Agent Screen
Neoplastic Transformation

Prior to assaying for the effect of ras oncogene expression on β-galactosidase production, $5 \times 10^5$ of the stably-transformed Rat-2 or Rat-6 cells were neoplastically transformed by transfecting the cells with 10 μg of plasmid pH06T1 DNA, as described above. Two days after transfection, the cells from one plate were split into 5 plates and grown for about 3 weeks. The medium was replaced with fresh medium every 3 days during this period, and the cultures were observed for the presence of multilayered cell foci. Such foci were then picked, cloned, expanded and assayed for β-galactosidase activity. The resulting cells are referred to as neoplastically transformed (or ras-transformed) below.

Effect of ras Transformation on β-Galactosidase Expression

Two-tenths-ml aliquots of DMEM with 10% fetal calf serum containing $1 \times 10^4$ Rat-6 cells which had been co-transfected with plasmids pαAP126 and pMAMneo (with and without further ras transformation) as described above were plated into the wells of 96-well microtiter plates and incubated at 37° C. in a humidified 5% $CO_2$ incubator. At various times after plating, the cells were analyzed for β-galactosidase activity, with the results shown in FIG. 3.

As shown in FIG. 3, Rat-6 cells stably transformed with plasmid pαAP126 but not further neoplastically transformed (Untransformed) showed a relatively high level of β-galactosidase activity, which increased over time as the cells multiplied. In contrast, β-galactosidase activity was initially suppressed in the cells which had also been neoplastically transformed (ras-transformed) and remained suppressed, despite continuing cell proliferation.

To determine whether the suppression of lacZ gene expression observed in the ras-transformed cells was due to an oncogene-mediated phenomenon, revertants of the neoplastically transformed cells were prepared essentially as described by Yanagihara et al. [*Oncogene* 5:1179 (1990)] and assayed for β-galactosidase activity.

Such revertants were prepared by treating 20 100-mm culture dishes, each of which contained $10^6$ Rat-6 cells which had been stably transformed with both plasmid pαAP126 and plasmid pH06T1, with 10 ml volumes of DMEM containing 5 μg/ml 5-azacytidine and 10% FCS for 24 hours at 37° C. Following this incubation, the medium was replaced with azacytidine-free DMEM with 10% FCS for a 24-hour recovery period, and then with the same medium containing 200 μg/ml cis-4-hydroxyproline.

This medium was replaced with fresh medium twice weekly for 3 to 4 weeks, after which colonies comprising apparently flat cells were marked and isolated using the agar overlay method. Such colonies were expanded in DMEM with 10% FCS and subcloned in microtiter plates. The cells in one revertant clone designated D-3 showed consistently flat morphology over several subpassages. Another clone designated D-3A was obtained by further subcloning of clone D-3.

Figure 4:
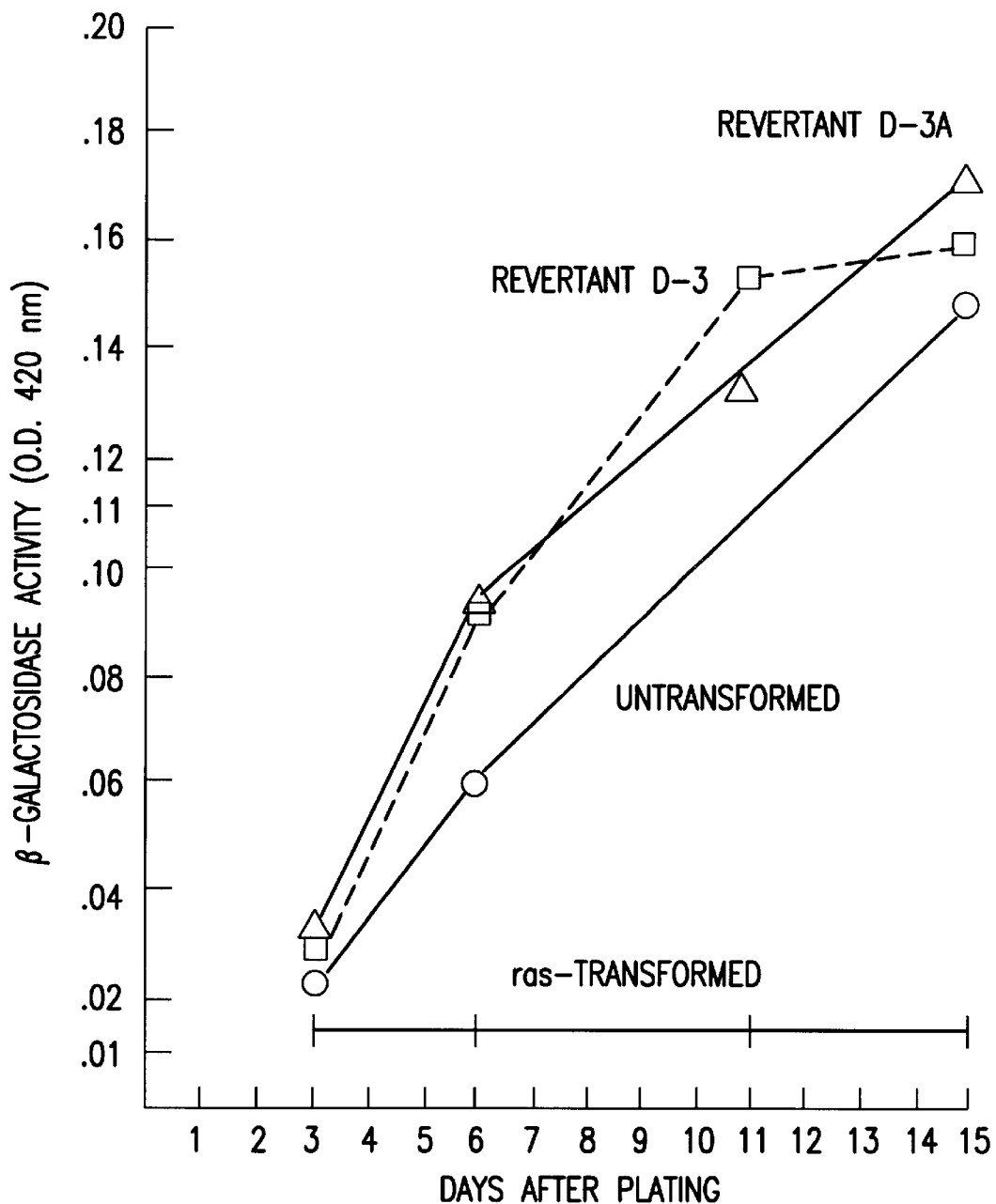
FIG. 4 is a graphical representation of the effect of neoplastic transformation upon β-galactosidase activity in Rat-6 cells that were stably transformed with plasmid pαAP126 and either neoplastically transformed with plasmid pH06T1 (ras-transformed) or not (Untransformed), or were revertants of such neoplastic transformation (Revertants D-3 and D-3A). β-Galactosidase activity (O.D. at 420 nm) is shown as a function of time after cell plating.

Revertant clones D-3 and D-3A were plated into microtiter plates, together with Rat-6 cells that had been stably transformed with plasmid pαAP126 and further neoplastically transformed with plasmid pH06T1 (ras-transformed) or not (Untransformed), and analyzed as described above at various times following plating for β-galactosidase activity. The results are shown in FIG. 4.

There, it can be seen that while the activity in the ras-transformed cells was suppressed as before, the activity in the cells from both revertant clones was similar to that of the untransformed cells. Suppression of lacZ gene expression was therefore dependent upon oncogene-mediated neoplastic transformation. Mutational revertants which no longer displayed the neoplastic phenotype showed release of the suppression at the human smooth muscle α-actin promoter.

That this release of suppression was specifically related to the reversal of oncogene-mediated neoplastic transformation has been shown by results obtained screening a substantial number of potential antineoplastic agents with the α-actin promoter/β-galactosidase/ras system. Agents shown by other tests to be generally cytotoxic which do not restore the normal cellular phenotype do not cause increased lacZ gene expression.

Growth Factor Antagonist Screen

Plasmid pαAP126 or pαAPI127 was co-transfected with plasmid pIBW into Rat-2 cells to produce stable transformant clones. G418-resistant colonies were isolated and expanded. A duplicate set of colonies was stained with X-gal substrate to identify colonies expressing β-galactosidase. In this way, clones stably incorporating plasmids pαAP126 and pαAPI127, designated Y2 and Z2, respectively, were isolated. A third clone designated SRαLacZ was similarly prepared using plasmid pSRαLacZ, a recombinant vector containing the lacZ gene of *E coli* operatively linked to an SRα promoter [Takebe et al., *Mol. Cell. Biol.* 3:280 (1983)]. Clone SRαLacZ was prepared as a control for nonspecific effects, because the SRα promoter is not responsive to growth factor-stimulated cell proliferation.

Growth factor assays were carried out by growing the above-mentioned stably transformed Rat-2 clones in DMEM containing 10% FBS and 200 μg/ml G418 antibiotic. The cells were seeded in 0.1 ml volumes of the medium into the wells of a 96-well microtiter plate (Becton Dickinson) at a density of $5 \times 10^4$ cells/well and incubated at 37° C. Twelve days after plating, various growth factors dissolved in DMEM containing 1 mg/ml bovine serum albumin (BSA) as a carrier were added. Samples containing various concentrations of potential growth factor antagonists dissolved in water or DMSO were added to some of the cultures, together with the growth factors.

Forty-eight hours after addition of the growth factors, the cells were lysed for 20 minutes at 4° C. with 0.05-ml aliquots of a 50 mM sodium phosphate solution (pH 7.0)

containing 5 mM β-mercaptoethanol and 0.5% Nonidet P-40 (octylphenolethylene oxide) detergent. After lysing the cells, 50 μl of LacZ reaction buffer containing 800 μg/ml CPRG in 50 mM sodium phosphate buffer (pH 7.0), 10 mM potassium chloride, 1 mM $MgSO_4$ and 50 mM β-mercaptoethanol were added to each well. The plates were incubated for 4 hours at 37° C., after which the reaction was terminated by the addition of 30 μl of a freshly-prepared solution of 1M $Na_2CO_3$. The absorbance of the solutions in the wells was measured at 590 nm.

To determine whether clone Z2 could respond to growth factor stimulation with a decreased level of β-galactosidase production, cells from the clone were plated, stimulated with various growth factors and then assayed for β-galactosidase activity. The growth factors tested included TGF-α and -β, PDGF-AA, EGF and bFGF, all over a concentration range of from 0 to 10 ng/ml of culture medium. The results are shown in FIG. 5.

Figure 5:
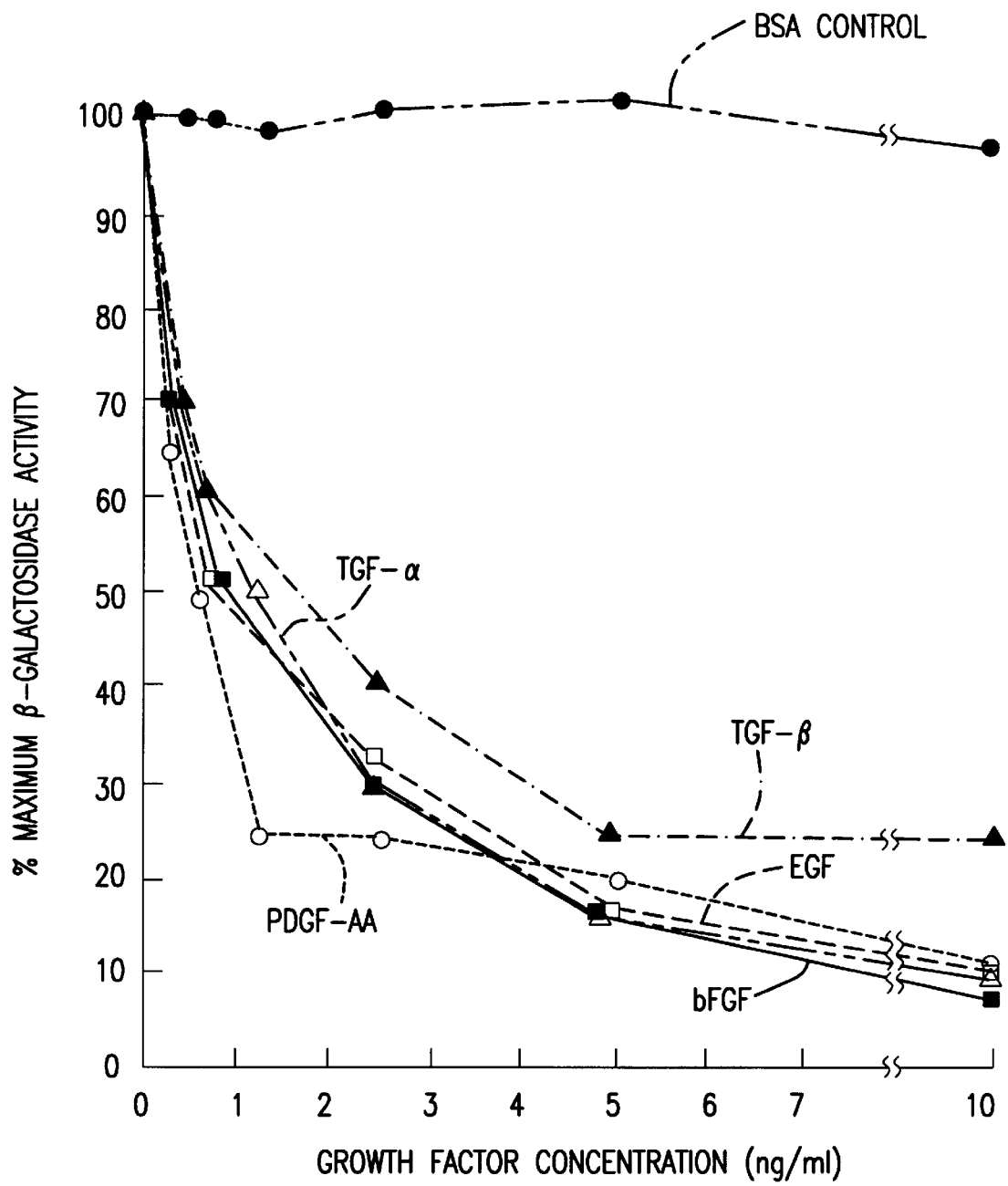
FIG. 5 is a graphical representation of the results of an assay for β-galactosidase activity in Rat-2 cells that were stably transformed with plasmid pαAPI127 and then treated with the indicated concentrations of bovine serum albumin (as a control) or one of the indicated growth factors. Percent maximal β-Galactosidase activity is shown as a function of protein concentration.

The data of FIG. 5 show that all of the growth factors tested caused a marked decrease in the level of β-galactosidase production, compared to the level observed in the control (carrier BSA only) cultures. Similar results were obtained using the Y2 clone transformed with plasmid pαAP126. In contrast, exposure of clone SRαLacZ to the same growth factors produced essentially no change in the level of lacZ expression.

As is also shown in FIG. 5, the median effective concentration for the various growth factors was about 1 ng/ml. This concentration is also known to be effective in inducing mitogenesis of fibroblast cells [ Corjay et al., *J. Biol. Chem.* 264:10501 (1989); LaRocca et al., *Cancer Cells* 2:106 (1990); Battegay et al., *Cell* 63:515 (1990)].

To demonstrate use of the foregoing system to detect a known growth factor antagonist, clone Z2 cells were plated and subjected to β-galactosidase assay as described above in the presence of TGF-α, TGF-β or PDGF-AA homodimer (all at a final concentration of 10 ng/ml) with or without neutralizing antibodies against PDGF (anti-PDGF) or control goat anti-human IgG antibodies (anti-IgG), both at a final concentration of 3 μg/ml. Controls were also run containing BSA carrier alone with or without one of the antibodies. The results are shown in Table 1.

TABLE 1

Antibody Antagonist Assay

| Growth Factor | Antibody | O.D. (590 nm) |
|---|---|---|
| — | — | 0.183 |
| — | Anti-PDGF | 0.180 |
| — | Anti-IgG | 0.180 |
| TGF-α | — | 0.022 |
| TGF-α | Anti-PDGF | 0.022 |
| TGF-α | Anti-IgG | 0.025 |
| TGF-β | — | 0.022 |
| TGF-β | Anti-PDGF | 0.171 |
| TGF-β | Anti-IgG | 0.025 |
| PDGF-AA | — | 0.022 |
| PDGF-AA | Anti-PDGF | 0.182 |
| PDGF-AA | Anti-IgG | 0.022 |

The data of Table 1 show that, as before, stimulation of the cells to proliferate by TGF-α, TGF-β and PDGF alone caused a marked reduction in β-galactosidase production. In the presence of neutralizing antibodies against PDGF, however, the levels of β-galactosidase activity produced by PDGF and TGF-β approximated control levels. The control anti-IgG antibodies had no effect.

The effect of the neutralizing anti-PDGF antibodies on the PDGF was expected; presumably the antibodies bound to the growth factor, thereby preventing its binding to the cellular receptors. The effect of these antibodies on TGF-β was not surprising, because it is believed that TGF-β-induced mitogenesis is an indirect effect which is mediated by PDGF [Moses et al., *Cell* 63:245 (1990)]. Moreover, TGF-β has been shown to induce both the PDGF A chain gene and c-sis, which encodes the PDGF B chain [Coffrey et al., *J. Cell. Physiol.* 132:143 (1987); Leof et al., *Proc. Natl. Acad. Sci.* USA 83:2453 (1986)]. The proliferative effects of TGF-α, on the other hand, appear to be direct, and not the result of intermediary PDGF activity.

As a further test of the utility of the methods of the invention to identify growth factor antagonists, the foregoing assay system was used with the growth factor antagonist, Suramin. Suramin is an organic compound that is capable of blocking growth factor-receptor interactions [La Rocca et al., *Cancer Cells* 2:106 (1990)].

This test was carried out by plating and subjecting clone Z2 cells to β-galactosidase assay as described above in the presence of EGF, TGF-α, TGF-β, bFGF and the PDGF-AA and PDGF-BB homodimers (all at a final concentration of 10 ng/ml) with or without 30 μM Suramin. Controls were also run containing BSA carrier alone with or without Suramin. The results are shown in Table 2.

TABLE 2

Antagonistic Effects of Suramin

| Growth Factor | Suramin | O.D. (590 nm) |
|---|---|---|
| — | − | 0.180 |
| — | + | 0.178 |
| TGF-α | − | 0.020 |
| TGF-α | + | 0.170 |
| TGF-β | − | 0.020 |
| TGF-β | + | 0.177 |
| PDGF-AA | − | 0.022 |
| PDGF-AA | + | 0.168 |
| PDGF-BB | − | 0.022 |
| PDGF-BB | + | 0.175 |
| EGF | − | 0.024 |
| EGF | + | 0.172 |
| bFGF | − | 0.024 |
| bFGF | + | 0.178 |

As shown in Table 2, Suramin strongly antagonized the effects of all of the growth factors tested.

Plasmid Deposit

*E. coil* strain DH5α harboring plasmid pαAPI127 was deposited Jul. 10, 1991 with the American Type Culture Collection (ATCC), Rockville, Md., and assigned Accession No. ATCC 68645. This deposit was made under the provisions of the Budapest Treaty on the International Recognition of the Deposit of Microorganisms for the Purposes of Patent Procedures.

Many modifications and variations of this invention can be made without departing from its spirit and scope, as will become apparent to those skilled in the art. The specific embodiments described herein are offered by way of example only, and the invention is to be limited only by the terms of the appended claims.

What is claimed is:

1. A method for identifying an antineoplastic agent comprising:
   (a) providing a mammalian cell line containing:
      (i) a recombinant vector comprising a reporter gene operatively linked to a genetic control element responsive to oncogene-mediated neoplastic transformation, the rate of expression of which reporter gene is measurably altered when the cell line undergoes such neoplastic transformation, and
      (ii) an oncogene, the expression of which renders the cell line neoplastically transformed;
   (b) contacting the neoplastically-transformed cell line of step (a) with a sample suspected to contain an antineoplastic agent; and
   (c) measuring the level of expression of the reporter gene, whereby an antineoplastic agent in the sample is identified by measurement of a level of expression of the reporter gene substantially similar to that of cells of the same cell line incubated in parallel which have been transformed by the vector of step (a)(i) but lack such oncogene and have not been exposed to the sample.

2. The method of claim 1 in which the cell line is stably transformed by the recombinant vector.

3. The method of claim 2 in which the oncogene is introduced into the cell line by a recombinant vector.

4. The method of claim 2 in which the oncogene is introduced into the cell line by a viral vector.

5. The method of claim 2 in which the oncogene is a latent oncogene activated by a chemical carcinogen or radiation.

6. The method of claim 2 in which neoplastic transformation of the cell line by the oncogene suppresses expression of the reporter gene.

7. The method of claim 2 in which the oncogene is a ras oncogene.

8. The method of claim 2 in which neoplastic transformation of the cell line by the oncogene increases expression of the reporter gene.

9. The method of claim 6 in which the genetic control element is a promoter selected from the group consisting of the rat thyroglobulin gene, the MCH class I gene, the human smooth muscle α-actin gene and the human MLC-2 isoform gene promoters.

10. The method of claim 9 in which the cell line is a Rat-2 cell line.

11. The method of claim 10 in which the genetic control element is the promoter of the human smooth muscle α-actin gene.

12. The method of claim 11 in which the genetic control element comprises DNA having a nucleotide sequence corresponding to the sequence of about base 1 to about base 910 of the sequence defined by SEQ ID NO:1.

13. The method of claim 12 in which the reporter gene is an $E$ $coil$ lacZ gene.

14. The method of claim 13 in which the recombinant vector is pαAP126 or pαAPI127.

15. The method of claim 8 in which the genetic control element is selected from the group consisting of the murine VL30 transcriptional element and the human β-polymerase promoter.

16. A mammalian cell line containing:
   (a) a recombinant vector comprising a reporter gene operatively linked to a genetic control element responsive to oncogene-mediated neoplastic transformation that is a promoter selected from the group consisting of the MCH class I gene, the human smooth muscle α-actin gene and the human MLC-2 isoform gene promoters, the rate of expression of which reporter gene is measurably altered when the cell line undergoes such neoplastic transformation, and
   (b) an oncogene, the expression of which renders the cell neoplastically transformed.

17. The cell line of claim 16 which is stably transformed by the recombinant vector.

18. The cell line of claim 16 which is a Rat-2 cell line.

19. The cell line of claim 16 in which the oncogene is a ras oncogene.

20. The cell line of claim 18 in which the genetic control element is a human smooth muscle α-actin promoter.

21. The cell line of claim 20 in which the genetic control element comprises DNA having a nucleotide sequence corresponding to the sequence of about base 1 to about base 910 of the sequence defined by SEQ ID NO:1.

22. The cell line of claim 20 in which the reporter gene is an $E.$ $coli$ lacZ gene.

23. The cell line of claim 22 in which the recombinant vector is plasmid pαAP126 or pαAPI127.

24. A method for identifying a growth factor antagonist comprising:
   (a) providing a mammalian cell line containing a recombinant vector comprising a reporter gene operatively linked to a genetic control element responsive to proliferation of the cell line, the rate of expression of which reporter gene is measurably decreased when the cell line is stimulated to proliferate by a growth factor;
   (b) contacting the cell line of step (a) with a quantity of a growth factor sufficient to stimulate proliferation of the cell line and with a sample suspected to contain an antagonist of the growth factor; and
   (c) measuring the level of expression of the reporter gene, whereby an antagonist of the growth factor in the sample is identified by measurement of a substantially increased level of expression of the reporter gene, compared to the level measured in cells of the same cell line incubated in parallel with the growth factor but without the sample.

25. The method of claim 24 in which the cell line is stably transformed by the recombinant vector.

26. The method of claim 25 in which the genetic control element is a human MCL-2 isoform gene promoter or a human smooth muscle α-actin promoter.

27. The method of claim 26 in which the mammalian cell line is a Rat-2 cell line.

28. The method of claim 27 in which the genetic control element is a human smooth muscle α-actin promoter.

29. The method of claim 28 in which the genetic control element comprises DNA having a nucleotide sequence corresponding to the sequence of about base 1 to about base 910 of the sequence defined by SEQ ID NO:1.

30. The method of claim 29 in which the reporter gene is an *E. coil* lacZ gene.

31. The method of claim 30 in which the recombinant vector is plasmid pαAP126 or pαAPI127.

32. A mammalian cell line containing a recombinant vector comprising a reporter gene operatively linked to a genetic control element responsive to proliferation of the cell line, the rate of expression of which reporter gene is measurably decreased when the cell line is stimulated to proliferate by a growth factor.

33. The cell line of claim 32 which is stably transformed by the recombinant vector.

34. The cell line of claim 33 in which the genetic control element is a human MCL-2 isoform gene promoter or a human smooth muscle α-actin promoter.

35. The cell line of claim 34 in which the mammalian cell line is a Rat-2 cell line.

36. The cell line of claim 35 in which the genetic control element is a human smooth muscle α-actin promoter.

37. The cell line of claim 36 in which the genetic control element comprises DNA having a nucleotide sequence corresponding to the sequence of about base 1 to about base 910 of the sequence defined by SEQ ID NO:1.

38. The cell line of claim 37 in which the reporter is an *E. coli* lacZ gene.

39. The cell line of claim 38 in which the recombinant vector is plasmid pαAP126 or pαAPI127.

40. Plasmid pαAP126 or pαAPI127.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 1127 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 1:

```
GAATTCGAGA  CGAGATTTGG  GTGGGGACGT  AGAACCAAAC  CATATCACCT  GGTCTCTCTA      60
CTTCCTGTCA  AGGAGGTTAG  TGGGCAGAGA  GGAGGGCTAC  AGAGGCTTCC  TTTGAACAAT     120
CTCCTTTCTT  TTCCAAACTA  CTTCTTTGAC  AGGCTGCTGG  GTAGACTCTC  TGGTCAAAGG     180
ATGGTCCCTA  CTTATGCTGC  TAAATTGCTC  GGTGACAAAT  TAGTAGACAA  AGCTAATGCA     240
CCAAAAAAAT  GAATGTAGTT  ATAGTAATGC  TAACATCCAA  ATTCCTCTTT  GTAAGACATA     300
GGCCTGTCAA  CCTTGTCTCC  ATACTTCAAT  TCCTATTTCC  ACTCACCTCC  CTCAAGAACT     360
TGATTTATAA  ACAGTGTGCC  TACCATAAAA  TCATCACTCC  CTCTATGTAT  TTATAGACGA     420
CTGAAGGAAT  ATCTTTCTTC  TTTGCATGCT  ACCGTGGTAG  AAGGGTTTTA  AAAGTCCGTG     480
CTAGGCAGAG  GCAGCCCTTT  CTGCCCCTTT  CTGTTCTCAG  TTTATTAGGA  AATGGCCTGA     540
AATTCCAGCA  TGATAGCAAG  CTGGCATCCT  CTGTGGAATG  TGCAAACCAT  GCCTGCATCT     600
GCCCATTACC  CTAGCTCAGT  GTCTCTGGGC  ATTTCTGCAG  TTGTTCTGAA  GGCTTGGCGT     660
GTTTATCTCC  CACAGGCGGC  TGAACCGCCT  CCCGTTTCAT  GAGCAGACCA  GTGGAATGCA     720
GTGGAAGAGA  CCCAGGCCTC  CGGCCACCCA  GATTAGAGAG  TTTTGTGCTG  AGGTCCCTAT     780
ATGGTTGTGT  TAGACTGAAC  GACAGGCTCA  AGTCTGTCTT  TGCTCCTTGT  TTGGGAAGCA     840
AGTGGGAGGA  GAGCAGGCCA  AGGGGCTATA  TAACCCTTCA  GCTTTCAGCT  TCCCTGAACA     900
CCACCCAGTG  TGGAGCAGCC  CAGCCAAGCA  CTGTCAGGGT  AAGTGGCGCC  AGGCCAAGGA     960
TGTGACTTAT  AGATTCCAGT  GGCTCTTTTA  ATTACCCGGT  ATAATAAGAC  ATCATCTGCA    1020
GGGATTTGGC  TGGGTTCATG  CACTGATATT  TCTGAATGAA  GATTGTACTA  CTAAAATGAT    1080
TGTAGCTTTT  GGCTTTAATG  ATCTAACGTT  AAAGACAGGG  CTAATAT                   1127
```

( 2 ) INFORMATION FOR SEQ ID NO: 2:

( i ) SEQUENCE CHARACTERISTICS:
        ( A ) LENGTH: 54 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 2:

```
CTGAGGCTGC  TTCCTCCCTG  TTTTCTATAG  AATCCTGTGA  AGCAGCTCCA  GCTG            54
```

( 2 ) INFORMATION FOR SEQ ID NO: 3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

-continued

```
GAATTCGAGA CGAATTT                                                17
```

( 2 ) INFORMATION FOR SEQ ID NO: 4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

```
CACACTGGGT GGTGTTC                                                17
```